(12) United States Patent
Lübbert et al.

(10) Patent No.: US 11,219,781 B2
(45) Date of Patent: Jan. 11, 2022

(54) ILLUMINATION FOR PHOTODYNAMIC THERAPY

(71) Applicant: BIOFRONTERA PHARMA GMBH, Leverkusen (DE)

(72) Inventors: Hermann Lübbert, Leverkusen (DE); Ben Novak, Leverkusen (DE); Markus Osterloh, Leverkusen (DE)

(73) Assignee: BIOFRONTERA PHARMA GMBH, Leverkusen (DE)

( * ) Notice: Subject to any disclaimer, the term of this patent is extended or adjusted under 35 U.S.C. 154(b) by 0 days.

(21) Appl. No.: 17/234,490

(22) Filed: Apr. 19, 2021

(65) Prior Publication Data
US 2021/0236843 A1 Aug. 5, 2021

Related U.S. Application Data

(63) Continuation of application No. 17/056,170, filed as application No. PCT/EP2019/064642 on Jun. 5, 2019.

(51) Int. Cl.
*A61N 5/06* (2006.01)
(52) U.S. Cl.
CPC ........... *A61N 5/0616* (2013.01); *A61N 5/062* (2013.01); *A61N 5/0624* (2013.01); *A61N 2005/0626* (2013.01); *A61N 2005/0663* (2013.01)

(58) Field of Classification Search
CPC .................................................. A61N 5/0616
See application file for complete search history.

(56) References Cited

U.S. PATENT DOCUMENTS 5,269,778 A 12/1993 Rink et al.
7,018,395 B2 * 3/2006 Chen .................. A61K 41/0057
607/88

(Continued)

FOREIGN PATENT DOCUMENTS

WO WO 2011/038923 A2 4/2011
WO WO 2015/028541 A1 3/2015

OTHER PUBLICATIONS

International Search Report and Written Opinion, dated Feb. 28, 2020, corresponding to International Application No. PCT/EP2019/064642 (filed Jun. 5, 2019), 16 pp.

*Primary Examiner* — Gary Jackson
*Assistant Examiner* — Zahed Kabir
(74) *Attorney, Agent, or Firm* — Leydig, Voit & Mayer, Ltd.

(57) ABSTRACT

An illumination system (1) for photodynamic therapy is provided, the illumination system comprising an illumination source (2), which is configured to emit an electromagnetic radiation (3) to illuminate a target surface (4) during operation, and an electronic control unit (5), wherein the illumination source is configured such that the intensity of the electromagnetic radiation emitted by the illumination source can be varied, wherein the electronic control unit is operatively connected to the illumination source and configured to control operation of the illumination source according to an illumination protocol during an illumination session performed with the illumination system, and wherein the illumination protocol comprises instructions to operate the illumination source during the illumination session in a plurality of different modes, the modes comprising: a) a first mode, wherein, in the first mode, the electronic control unit controls operation of the illumination source such that the intensity of the electromagnetic radiation emitted by the illumination source is increased continuously (Continued)

or quasi-continuously from a base intensity B to a target intensity T within a first mode time interval, b) a second mode, wherein, in the second mode, the electronic control unit controls operation of the illumination source such that the intensity of the electromagnetic radiation emitted by the illumination source is constant or substantially constant for a second mode time interval, and c) a third mode, wherein, in the third mode, the electronic control unit controls operation of the illumination source such that the illumination source is operated such that darker phases and illumination phases alternate for a third mode time interval, wherein the intensity of the electromagnetic radiation emitted by the illumination source is lower in the darker phases than in the illumination phases, or wherein, in the darker phases the illumination source does not emit electromagnetic radiation whereas the illumination source emits electromagnetic radiation in the illumination phases. Furthermore, a computer program product and a kit for treating a disease are provided and a method for operating an illumination source and a method for treating a skin disease.

14 Claims, 2 Drawing Sheets

(56) References Cited

U.S. PATENT DOCUMENTS

| | | | |
|---|---|---|---|
| 2002/0173833 A1* | 11/2002 | Korman | A61K 41/0071 607/88 |
| 2004/0111132 A1* | 6/2004 | Shenderova | A61N 5/0616 607/88 |
| 2005/0024853 A1 | 2/2005 | Thomas-Benedict | |
| 2014/0207211 A1 | 7/2014 | Lee et al. | |
| 2015/0005692 A1* | 1/2015 | Barolet | A61K 31/375 604/20 |
| 2016/0199664 A1* | 7/2016 | Hogset | A61N 5/062 604/20 |

\* cited by examiner

ILLUMINATION FOR PHOTODYNAMIC THERAPY

CROSS-REFERENCE TO RELATED APPLICATIONS

This application is a continuation of U.S. application Ser. No. 17/056,170, filed on Nov. 17, 2020 which application is a 371 U.S. National Phase of International Application Serial No. PCT/EP2019/064642, filed Jun. 5, 2019, each of which is hereby incorporated by reference in its entirety.

BACKGROUND OF INVENTION

This disclosure relates to an illumination system for photodynamic therapy, the illumination system comprising an illumination source, which is configured to emit an electromagnetic radiation to illuminate a target surface during operation, and an electronic control unit.

The disclosure also relates to a method for operating an illumination source, a computer program product, such as a data carrier, a kit for treating a disease and a method for treating a skin disease.

SUMMARY OF THE INVENTION

Photodynamic therapy (PDT) has been widely studied and several approaches have been used successfully for treatment. In general there are three requirements for PDT: a photosensitizer, molecular oxygen and light of a specific wavelength. For dermatological PDT usually a prodrug, for example aminolevulinic acid (ALA), is topically applied to the skin. Subsequently, the prodrug is then converted by the cells, e.g. by neoplastic cells, into the actual photosensitizer. The molecular mechanism of action in PDT is based on cellular ALA uptake, synthesis and accumulation of the photosensitizer, which can be excited by light of specific wavelengths leading to the formation of reactive oxygen species (ROS), upon the presence of oxygen. The ROS can initiate cell death, e.g. in the form of apoptosis, necrosis and autophagy.

However, one of the major issues that hinder broad acceptance of PDT by patients is the relatively high amount of pain perceived by the patients during the illumination which ranges from mild inconvenience to severe pain to a point where the treatment has to be aborted. In addition, although PDT is a highly effective treatment method, reoccurrence of some diseases like actinic keratosis is common and thus patients often, although having been successfully treated, later develop different lesions at different skin areas and again require medical intervention. Moreover, some patients are not completely cured after a single PDT session and require a second session. If the first PDT they received was very painful the chances of beginning or completing a second PDT are small despite the fact that it offers supreme efficacy compared to other therapy options. As a result, the acceptance of many patients to undergo treatment or re-treatment decreases. This of course has great negative implications for an individual PDT and PDT as a whole.

Consequently, pain reduction is of crucial interest to increase acceptance levels of PDT treatment as a whole, thus increasing the use of this superior treatment.

Nevertheless, PDT efficacy is also limited by any of the involved factors, i.e. photosensitizer, oxygen, and light. Reduced availability of any of these factors may hamper with ROS formation. Optimized pharmaceutical forms, pre-treatments and incubation modalities can ensure proper and abundant deposition of the photosensitizer. Still, light has to reach a molecule in sufficient quantities and oxygen needs to be present as an energy acceptor.

In particular the light of the illumination at the appropriate wavelength to activate the respective photosensitizer needs to be made available at a sufficient dose. For topical applications, a frequently used photosensitizer is protoporphyrin IX (PpIX), mostly produced in skin cells by application of a precursor molecule, such as ALA. PpIX can be activated by light of a variety of different wavelengths of which red (approx. 635 nm), blue (approx. 420 nm), yellow (approx. 542 nm) or green (approx. 506 nm) light are most frequently used. Generally, a light dose received by a target, e.g. the treated skin, depends on three main factors. The irradiance provided by the light source, the distance between the target area and the light source, and the duration of the illumination.

The current practice is to apply the entire light dose within a short interval (e.g. ranging from 7 to 12 minutes with red light or 15-20 minutes with blue light). Usually, this approach is limited by the occurrence of pain. Moreover, photobleaching of the photosensitizer may occur to a greater extent at higher light intensities and may limit the treatment efficiency. Photobleaching describes the effect that the photosensitizer is inactivated by permanent disruption of its chemical structure, e.g. by cleavage of covalent bonds. This photobleaching effect may coincide with temporal oxygen depletion in the target tissue due to a massive initial reaction. This leads to a rapid decrease in oxygen, which is required for ROS formation. All photobleaching that occurs during the phase where oxygen is limited is likely to be unproductive, as it yields fewer cytotoxic singlet oxygen.

It should be noted that the statements above should not be construed as being admitted prior art. They are only made to illustrate the background of the presently disclosed concepts and may not have been made available to the public yet.

It is an object of the invention to provide an improved illumination system for photodynamic therapy, an improved method for operating an illumination source, an improved computer program product, such as a data carrier, an improved kit for treating a disease, and/or an improved method for treating a skin disease, which preferably allow or are configured to limit the pain burden, expediently while maintaining an acceptable effectiveness of the therapy, and/or which allow or are configured to increase the effectiveness of the therapy.

The respective object may, inter alia, be achieved by the subject matter of the independent claims. Advantageous embodiments and refinements are the subject matter of the dependent claims. However, further advantageous concepts may be disclosed herein besides the ones which are currently claimed.

One aspect of the present disclosure relates to an illumination system for photodynamic therapy, wherein the illumination system comprises an illumination source, which is configured to emit an electromagnetic radiation to illuminate a target surface during operation, and an electronic control unit. The illumination source is configured such that the intensity of the electromagnetic radiation emitted by the illumination source can be varied, wherein the electronic control unit is operatively connected to the illumination source and configured to control operation of the illumination source according to an illumination protocol during an illumination session performed with the illumination system, and wherein the illumination protocol comprises instructions to operate the illumination source during the illumination session in a plurality of different modes, the modes comprising:

a) a first mode, wherein, in the first mode, the electronic control unit controls operation of the illumination source such that the intensity of the electromagnetic radiation emitted by the illumination source is increased continuously or quasi-continuously from a base intensity B to a target intensity or a targeted intensity T within a first mode time interval, b) a second mode, wherein, in the second mode, the electronic control unit controls operation of the illumination source such that the intensity of the electromagnetic radiation emitted by the illumination source is constant or substantially constant for a second mode time interval, and/or c) a third mode, wherein, in the third mode, the electronic control unit controls operation of the illumination source such that the illumination source is operated such that darker phases and illumination phases alternate for a third mode time interval, wherein the intensity of the electromagnetic radiation emitted by the illumination source is lower in the darker phases than in the illumination phases, or wherein, in the darker phases the illumination source does not emit electromagnetic radiation whereas the illumination source emits electromagnetic radiation in the illumination phases. The control unit may be configured to control the operation voltage and/or the operation current provided to the illumination source in a manner which results in operation of the illumination source as desired for the respective mode.

The proposed illumination system may limit or reduce the perceived pain burden. This is achieved, inter alia, by operating the illumination source during the illumination session in the above-mentioned different modes as will be explained in more detail below. The proposed illumination system and particularly the illumination protocol may increase the effectiveness of the PDT. Thus, the proposed system and/or the protocol may provide for a pain optimized yet still efficient therapy.

In the first mode the intensity of the electromagnetic radiation emitted by the illumination source is increased continuously or quasi-continuously from a base intensity B to a target intensity T. The term "quasi-continuously" may mean that the intensity of the emitted radiation is constant for a maximum duration less than or equal to one of the following values: 5 s, 4 s, 3 s, 2 s, 1 s or 500 ms. The term "continuously" may mean that the intensity of the emitted radiation is constant for a maximum duration less than the values associated with "quasi-continuously", preferably less than or equal to one of the following values: 400 ms, 300 ms, 200 ms, 100 ms, 50 ms, 25 ms, 20 ms, 15 ms, 10 ms, 5 ms, 4 ms, 3 ms, 2 ms, 1 ms. As the emitted intensity is characterized or determined by the electrical energy provided to the illumination source, according values may be characteristic for the operation voltage and/or current being increased continuously or quasi-continuously.

The continuous or quasi-continuous increase in intensity may lead to a moderate reaction onset. The increase in intensity may reduce initial photobleaching and/or promote re-oxygenation of the treated skin. Apart from that, the continuous increase of the irradiance may trigger a sufficient photodynamic effect, including initial inflammatory reactions that induce vasodilation for even better oxygen supply, wherein the photodynamic effect describes the process during PDT which leads to the destruction of cells. Therefore, the efficiency of the treatment during the first mode may be ensured.

Another advantage of the first mode is that the continuous increase of the irradiance on the skin—the irradiance on or of the skin depends on the emitted intensity as well as on the distance between the illumination source and the skin—allows adaptation of the sensory nerve endings in the skin to the stimulus, which balances pain sensation and ultimately leads to a reduced pain burden in patients. A slow increase of the irradiance over an interval of between 4 to 10 minutes has proven to be acceptable.

In the second mode the intensity of the electromagnetic radiation emitted by the illumination source is constant or substantially constant. The term "substantially constant" may mean a maximum deviation from an intensity I of less than or equal to one of the following values: 15%, 10%, 5%. I is the constant intensity during the second mode. I may be equal to T.

The constant or substantially constant intensity of the electromagnetic radiation in the second mode may provide comparatively high irradiance, preferably in a short time span. It may assist in or be responsible for sustaining a lasting photodynamic effect, preferably without causing unbearable pain burden, e.g. due to its limited duration.

In the third mode the illumination source is operated such that darker phases and illumination phases alternate. The darker phases may allow the neuronal activation to wear off to some extent, which leads to a lower pain burden. The illumination phases may allow to achieve a targeted light dose for the illumination session. In the illumination phases, the intensity is expediently greater than in the darker phases. In the darker phases, the illumination source may be operated to emit a lower intensity or not emit radiation at all.

Moreover another advantage of the third mode may be the balanced rate of oxygen consumption and oxygen resupply. The resupply of oxygen in the darker phases may expediently support the efficiency of the treatment by preventing late oxygen depletion.

Therefore, a combination of the first, second and third modes may lead to

- a moderate reaction onset, to reduce the pain burden and to reduce initial photobleaching and promote re-oxygenation of the treated tissue,
- a sufficient photodynamic effect, including initial inflammatory reactions that induce vasodilation for even better oxygen supply,
- re-oxygenation and thus additional photosensitizer activation, especially in the later phases of the illumination, e.g. when higher or high fluence rates are used, in order to prevent late oxygen depletion, and
- a therapy duration which is increased only moderately or not at all for achieving a given light dose on the irradiated target while maintaining an effective light dose without creating an unbearable pain burden.

In an embodiment B may be less than or equal to one of the following values: 0.5 T, 0.45 T, 0.4 T, 0.35 T, 0.3 T. Alternatively or additionally, B may be greater than or equal to one of the following values: 0.1 T, 0.15 T, 0.2 T, 0.25 T, 0.3 T. Thus, B may be between 0.1 T and 0.5 T or any other range formed by combining values of the two listings.

Choosing B accordingly may allow for a sufficient adaptation of the sensory nerve endings in the skin to the stimulus, which may balance pain sensation. This may lead to a reduced pain burden. In addition, a sufficient photodynamic effect may be achieved or triggered. Higher values of B, e.g. greater than 0.6 T may cause too much initial pain during the illumination session. Values below 0.1 T may be insufficient to trigger a substantial photodynamic effect and/or lead to instable illumination due to technical restrictions.

In an embodiment the constant or quasi-constant intensity during the second mode may be the target intensity T in the first mode. This may allow a direct transition from the first mode to the second mode. It is advantageous that the efficiency of the treatment is not jeopardized by varying the intensity once the target intensity has been reached. In addition, a direct transition from the first to the second mode leads to less irritation of the nerves of the patient and thus may also lead to a lower pain burden.

In an embodiment the intensity during the illumination phases may be T. This may result in a reduced pain burden because the nerves may have been already adapted to T, e.g. from the preceding mode(s) of the illumination protocol.

In an embodiment the maximum intensity during the first mode, the second mode, and the third mode may be T. This, likewise, may lead to less irritation of the nerves of the patient and thus also contribute to a lower pain burden.

In an embodiment the intensity may be increased in the first mode linearly from B to T. A linear increase may cause that the patient feels comfortable as he can easily adjust to the rate of pain increase and the increase may be more predictable.

In an embodiment the intensity may be increased in the first mode strictly monotonously. Stepwise increases in intensity are much more noticeable to the patient than a strictly monotonous increase in intensity. Consequently, a strictly monotonous increase of intensity leads to less pain.

In an embodiment the intensity may be increased non-linearly in the first mode. At the beginning or the start of the first mode the intensity may be increased at a slower rate than later on in the first mode. This may cause the beneficial effects of the photodynamic effect to appear earlier, wherein an initial phase for adaptation of the nerves and the intensity is retained.

In an embodiment, the illumination protocol comprises a priming mode. The priming mode may be a mode of operation of the illumination source which precedes the first mode. In the priming mode of operation, the intensity of the electromagnetic radiation emitted by the illumination source may be constant or substantially constant for a priming mode time interval. The intensity in the priming mode may be P. P may be less than or equal to B, i.e. the base intensity in the first mode. The subject/patient irradiated using the protocol can become accustomed to the irradiance during an initial operation of the illumination source in the priming mode. When the priming mode is applied, the intensity in the first mode subsequent to the priming mode may be increased linearly and/or with a higher rate than without the priming mode, preferably without significantly raising the perceived pain for the user.

In an embodiment the illumination source may be operated in the first mode before it is operated in the second mode and/or before it is operated in the third mode during the illumination session. The first mode may be to adapt the nerves to the radiation intensity or the pain burden during the illumination session. For this purpose, the first mode preferably initially uses a low intensity. In order to reduce the sensation of pain, it may therefore be advantageous to perform the first mode before further modes, e.g. modes which may feature a higher intensity than the initial light intensity, e.g. B, of the first mode.

In an embodiment the illumination source may be operated in the second mode after the first mode and/or before the third mode during the illumination session. Since the second mode may have a constant intensity, it is advantageous for reducing pain when the second mode is preceded by the first mode, which may serve to adapt the nerves to the light intensity of the second mode. Moreover, it is also expedient to have the mode with the constant intensity (second mode) between the increasing intensity (first mode) and the alternating illumination and darker phases (third mode), as the second mode may be the one where the pain burden is highest. The following darker and illumination phases may render the higher pain in the intermediate portion of the illumination session less significant for the user. The user may preferably remember the moderate pain during the third mode and the low initial pain.

In an embodiment the beginning of the operation of the illumination source in the first mode may define the start of the illumination session and the end of the operation of the illumination source in the third mode may define the end of the illumination session. If the priming mode is applied, the beginning of the operation of the illumination source in the priming mode may define the beginning of the illumination session.

In an embodiment every mode selected from the first mode, the second mode, and the third mode of operation of the illumination source may occur once, preferably only once, during the illumination session. Thus, the overall duration may be kept below 16 minutes, which is considered acceptable by most patients and physicians, e.g. in terms of pain burden and time consumption. This duration may include or exclude the operation in the priming mode.

In an embodiment the illumination system may have a target location or may define a target location in which the target surface is to be arranged relative to the illumination source during the illumination session. The target location (i.e. the position of the target surface relative to the illumination source) may be defined by a bearing surface, which is contacted by a section of the user's head, e.g. by the forehead or the chin. The section of the user's head may stay in contact with the bearing surface during the entire session. The target location may be arranged at a distance from a radiation exit surface of the illumination source. A gaseous medium may be present between the radiation exit surface of the illumination source, e.g. a surface of an optical element, e.g. a diffusor or a lens, and the target surface and/or the target location.

The term "target surface" as used herein may refer to a surface that is to be illuminated by the electromagnetic radiation emitted by the illumination source.

The term "target location" as used herein may refer to the position of the target surface relative to the illumination source. In other words, the target location may be a location which is determined by the design of the illumination device. The target location may be the position in which the surface which is to be illuminated should be arranged relative to the illumination device during operation of the device, i.e. during the illumination session. For example, in the target location, the radiation generated by the illumination device may have a desired irradiance distribution, e.g. along the target surface. If the target surface were arranged in a different location relative to the illumination source the irradiance distribution may be different and/or may not be suitable for the desired purpose.

The term "bearing surface" as used herein may refer to a surface that is suitable to support a user's body part, such as the head, during an operation, preferably in the target location. The body part may comprise the target surface which should be illuminated using the illumination device. The bearing surface may be formed by a mechanical support.

In an embodiment the distance between the radiation exit surface of the illumination source and the target location may be less than or equal to one of the following values: 20 cm, 15 cm 10 cm, 8 cm, 7 cm, 6 cm, 5 cm. Alternatively or additionally, the distance between the radiation exit surface of the illumination source and the target location may be greater than or equal to one of the following values: 1 cm, 2 cm, 3 cm, 4 cm, 5 cm. The distance between the radiation exit surface of the illumination source and the target location may be between 1 cm and 20 cm, preferably between 5 cm and 8 cm.

PDT efficacy is potentially limited by any of the involved factors, i.e. photosensitizer, oxygen, and light dose. Generally, the light dose received by a target, e.g. the treated skin, depends on three main factors. One of it is the distance between the target surface and the light source. The distance has a direct influence on the light dose received by a target, as the intensity at a specific location depends on the distance of that location from the illumination source. A distance between 1 cm and 20 cm, preferably between 5 cm and 8 cm, is advantageous because it can optimally unfold the effect of PDT. Furthermore, the perceived pain may be acceptable for patients in the distances specified above, especially for the typically applied irradiances.

In an embodiment the illumination source may comprise at least one optoelectronic semiconductor chip for generating the electromagnetic radiation, e.g. a light-emitting diode chip. This allows a reliable, cost effective and accurate implementation of the illumination source. Optoelectronic chips allow tuning the emission wavelength easily to a required (peak) wavelength, e.g. by appropriately engineering the active region of the chip, e.g. by band-gap engineering. Thus, electrical energy may be efficiently converted into radiation energy in the relevant wavelength range.

In an embodiment the radiation emitted by the illumination source may be incoherent radiation. As compared to coherent radiation, incoherent radiation is easier to handle.

In an embodiment the radiation emitted by the illumination source may be monochromatic, e.g. of light of one specific color.

In an embodiment the electromagnetic radiation may have a peak wavelength in the visible spectral range, e.g. in the red, blue, green, or yellow spectral range.

In an embodiment the electromagnetic radiation has a peak wavelength in the red spectral range (in the following also referred to as "red light"). The peak wavelength of the illumination source may be greater than 500 nm, greater than 600 nm, or greater than 630 nm. The peak wavelength may be less than 700 nm. The peak wavelength may be 635 nm. Red light has the advantage that it can reach regions in the body which are further away from the skin with a high intensity more easily than light of a shorter wavelength, which is subject to a more pronounced absorption than red light in the body tissue. Accordingly, the present disclosure uses red light as an example.

In an embodiment the illumination system may be configured to irradiate the target surface with a predetermined light dose during the illumination session. The light dose may be greater than or equal to one of the following values when the target surface is arranged at the target location relative to the illumination source during the illumination session: 30 $J/cm^2$, 35 $J/cm^2$, 37 $J/cm^2$. Alternatively or additionally, the light dose may be less than or equal to one of the following values when the target surface is arranged at the target location relative to the illumination source during the illumination session: 45 $J/cm^2$, 40 $J/cm^2$, 37 $J/cm^2$. The values above particularly hold at least for red light.

A sufficient light dose is one of the key requirements to successfully carry out PDT. However, when choosing the light dose, the maximum tolerable level of pain for the patient must also be taken into account. The range between a light dose of 30 and 45 J/cm2, in particular a light dose of 37 $J/cm^2$, may be considered the best compromise between adequate treatment efficiency and pain burden, e.g. when using red light.

In another embodiment the electromagnetic radiation has a peak wavelength in the blue spectral range (in the following also referred to as "blue light"). The peak wavelength of the illumination source may be between 400 nm and 490 nm, e.g. 420 nm.

In an embodiment the illumination system may be configured to irradiate the target surface with a predetermined light dose during the illumination session. The light dose may be greater than or equal to one of the following values when the target surface is arranged at the target location relative to the illumination source during the illumination session: 8 $J/cm^2$, 9 $J/cm^2$, 10 $J/cm^2$. Alternatively or additionally, the light dose may be less than or equal to one of the following values when the target surface is arranged at the target location relative to the illumination source during the illumination session: 12 $J/cm^2$, 11 $J/cm^2$, 10 $J/cm^2$. The values above particularly hold at least for blue light.

The range between a light dose of 8 and 12 $J/cm^2$, in particular a light dose of 10 $J/cm^2$, may be considered the best compromise between adequate treatment efficiency and pain burden, e.g. when using blue light.

It should be noted that yellow or green light could also be used. This is particularly true if ALA is used as prodrug as the photosensitizer PpIX does not only absorb red and/or blue light, but also green and/or yellow light.

In an embodiment the first mode time interval, the second mode time interval, and/or the third mode time interval may be greater than or equal to one of the following values: 1 min, 1.5 min, 2 min, 2.5 min, 3 min, 3.5 min, 4 min, 4.5 min, 5 min. Alternatively or additionally, the first mode time interval, the second mode time interval, and/or the third mode time interval may be less than or equal to one of the following values: 10 min, 9.5 min, 9 min, 8.5 min, 8 min, 7.5 min, 7 min, 6.5 min, 6 min, 5.5 min, 5 min.

In an embodiment the first mode time interval and/or the second mode time interval may be shorter than the third mode time interval. Thus, the third mode may provide the greatest contribution to the total light dose delivered to the target surface during the illumination session.

In an embodiment, the priming mode time interval may be shorter than the first mode time interval, the second mode time interval and/or the third mode time interval.

In an embodiment the priming mode time interval may be less than or equal to one of the following values: 4 min, 3 min, 2 min, 1 min. Alternatively or additionally, the priming mode time interval may be greater than or equal to one of the following values: 10 s, 20 s, 30 s, 1 min.

In an embodiment the first mode time interval may be shorter than the second mode time interval. In this way, the illumination duration with an intensity less than T may be kept comparatively small. Thus, the session duration is not unnecessarily extended.

In an embodiment the first mode time interval and/or the second mode time interval may be longer than the duration of a single darker phase and/or a single illumination phase, preferably at least 5 d, 6 d, 7 d, 8 d, 9 d, 10 d, 11 d, 12 d, 13 d, 14 d, 15 d, where d is the duration of one single darker phase and/or of one single illumination phase.

In an embodiment the duration of one darker phase and/or of one illumination phase may be less than or equal to one of the following values: 60 s, 50 s, 45 s, 40 s, 35 s, 30 s, 25 s, 20 s. Alternatively or additionally, the duration of one darker phase and/or of one illumination phase may be greater than or equal to one of the following values: 15 s, 20 s, 25 s, 30 s. Phase durations in the range between 15 and 60 seconds may be advantageous to take advantage of the positive effects without increasing the duration of treatment unnecessarily.

In an embodiment the durations of different darker phases in the third mode may be equal. In an embodiment the durations of different illumination phases in the third mode may be equal. In an embodiment the durations of the darker phases may be constant and may be equal to or different from the duration of the illumination phases.

In an embodiment the duration of the darker phases may be less than the duration of the illumination phases. This results in shorter interruptions of the illumination during the third mode, which may contribute to keep the session duration at a desired time.

In an embodiment, the duration of the second mode time interval and/or the duration of the first mode time interval and the second mode time interval when taken together is less than or equal to one of the following values: 12 min, 11 min, 10 min, 9 min, 8 min. Thus, the first pain relief, e.g. by a darker phase in the third mode after the second mode, may occur at a time when or before the patient experiences the highest pain. Patients have been reported to perceive the highest pain or unbearable pain after about 10 minutes during PDT sessions, for example. Therefore, keeping the second mode or the combination of first and second mode taken together below 10 minutes may be beneficial with respect to pain management.

In an embodiment the duration of the entire illumination session may be less than or equal to one of the following values: 20 min, 19 min, 18 min, 17 min, 16 min, 15 min, 14 min, 13 min. Session durations up to 20 minutes are usually accepted by users without problems.

In an embodiment the duration of the entire illumination session may be greater than or equal to one of the following values: 10 min, 11 min, 12 min, 13 min. The duration of the session may be between 10 min and 20 min, for example.

In an embodiment the intensity during each illumination phase in the third mode may be the same.

In an embodiment the intensity during the darker phases may be less than or equal to B or is equal to zero. Therefore, the re-supply with the oxygen may be facilitated in the dark phases.

In an embodiment the intensity in a single illumination phase may be constant or substantially constant. A constant or substantially constant intensity in a single illumination phase contributes to a more predictable photodynamic effect.

In an embodiment the intensity may vary between different illumination phases. Variation of different intensities may be helpful to adjust the patient's pain burden or load even more during treatment. For example, at the beginning of the third mode, the intensity in the illumination phase may be higher than near the end of the third mode.

In an embodiment the illumination protocol may govern the entire illumination session.

Another aspect of the present disclosure relates to a method for operating an illumination source, wherein the illumination source is operated according to an illumination protocol, e.g. during an illumination session performed with the above described illumination system, and wherein the illumination protocol comprises instructions to operate the illumination source during the illumination session in the above described different modes.

In addition, the disclosure also relates to a computer program product, such as a data carrier, e.g. a non-transitory data carrier, or data stream, the computer program product containing machine readable instructions which, in particular when loaded in and/or executed by a computer system, e.g. by an electronic control unit thereof, cause an illumination source to operate according to the above mentioned protocol.

Moreover, another aspect relates to a kit for treating a disease, e.g. a skin disease, such as a neoplastic skin disease. The kit may comprise a pharmaceutical substance suitable to be topically applied to the skin in a region to be treated and an illumination system as mentioned above, wherein the illumination system is configured to irradiate a region of the skin to which the substance has been applied.

In an embodiment the pharmaceutical substance may be a photosensitizing drug or precursor to such a drug that is excitable by light in the emitted spectrum.

In an embodiment the pharmaceutical substance may comprise 5-aminolevulinic acid. 5-aminolevulinic acid has been well studied and is considered a reliable prodrug for generating a photosensitizer.

Yet another aspect relates to a method for treating a skin disease comprising the following steps: applying a pharmaceutical substance to the surface of the skin in a region which is to be treated; irradiating the region with an illumination source according to the method as specified above and/or using the illumination system as specified above.

In an embodiment the illumination system, the kit and/or the method may be used to treat a skin disease or disorder. The skin disease or disorder may be or may comprise a neoplastic skin disease, like actinic keratosis, basal cell carcinoma, squamous cell carcinoma in situ, warts, acne, wound healing disorders/chronic wounds, bacterial and/or fungal infections or inflammatory skin diseases.

It should be noted that the present disclosure covers non-therapeutic methods.

Due to the low pain burden, the illumination system can be used universally for the treatment of various diseases.

Of course, features described above in connection with different aspects and embodiments may be combined with each other and with features described below. Thus, features relating to the system do also apply for the methods and the kit and vice versa.

Further features and refinements become apparent from the following description of the exemplary embodiments in connection with the accompanying figures.

DETAILED DESCRIPTION OF THE INVENTION

Figure 1:
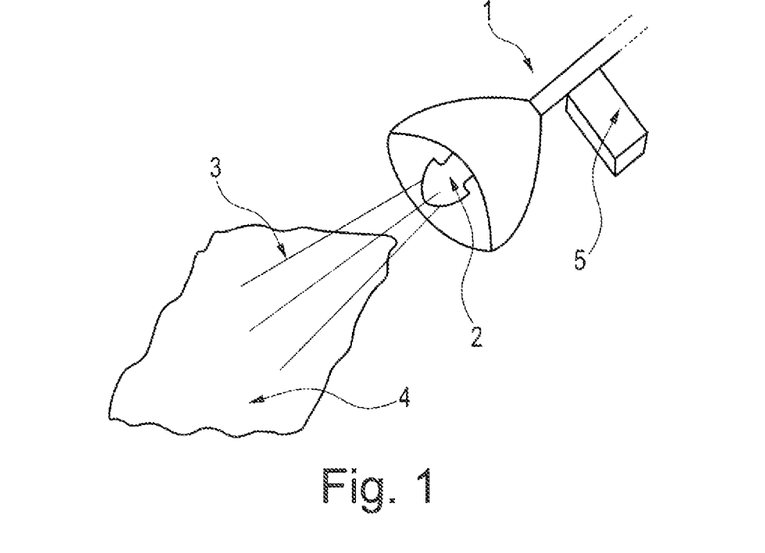
FIG. 1 schematically shows a perspective view of an illumination system and a target surface.

FIG. 1 shows an illumination system 1, e.g. for photodynamic therapy (PDT). The illumination system 1 comprises an illumination source 2, which is configured to emit an electromagnetic radiation 3 to illuminate a target surface 4 during operation, and an electric control unit 5. The target surface 4 may be a human skin, for example the skin on a head or another region to be treated. Furthermore, a PDT requires a photosensitizer and molecular oxygen (not explicitly shown). Usually the photosensitizer is obtained by a prodrug (not explicitly shown) which is topically applied to the skin, expediently in the target region, and which is then converted by the cells, preferably by neoplastic cells, into the actual photosensitizer. The prodrug may be 5-aminolevulinic acid (5-ALA), an endogenous precursor for heme biosynthesis.

The molecular mechanism of action in PDT is based on cellular aminolevulinic acid uptake, synthesis, and accumulation of the photosensitizer, which is excited by light of specific wavelengths leading to the formation of reactive oxygen species (ROS), upon the presence of oxygen. These ROS species can initiate cell death in the form of apoptosis, necrosis and/or autophagy.

The illumination source 2 is configured such that the intensity of the electromagnetic radiation 3 emitted by the illumination source 2 and/or the one reaching the target surface 4 can be varied. Moreover, it is possible that the distance between the target surface 4 and the illumination source 2 of the illumination system 1 is adjustable and thus variable. It is, however, preferred, that the target surface 4 has a fixed position relative to the illumination source.

The illumination source 2 may comprise a light-emitting diode (LED) or a plurality of light-emitting diodes. In particular illumination sources such as the ones distributed by the company Biofrontera AG under the tradename BF-RhodoLED® are suitable. The light emitted by the light-emitting diodes promotes the formation of reactive oxygen species (ROS). The wavelength of the light emitted by the illumination source may be greater than 400 nm, greater than 500 nm or greater than 600 nm. For example, the wavelength may be 635 nm, i.e. radiation in the red spectral range. As another example, the wavelength may be 420 nm, i.e. radiation in the blue spectral range. Alternatively, yellow or green radiation may also be applicable to activate the photosensitizer appropriately.

The illumination system 1 may have a target location or may define a target location in which the target surface 2 is to be arranged relative to the illumination source 2 during the illumination session. The target location may be defined by a bearing surface which is contacted by a section of the user's head, e.g. by the forehead or the chin. The section may stay in contact with the bearing surface during the entire session. The target location may be arranged at a distance from a radiation exit surface of the illumination source 2. A gaseous medium may be present between the radiation exit surface of the illumination source 2, e.g. a surface of an optical element, e.g. a diffusor or a lens, and the target surface 4 and/or the target location.

The distance between the radiation exit surface of the illumination source 2 and the target location may be less than or equal to one of the following values: 20 cm, 15 cm 10 cm, 8 cm, 7 cm, 6 cm, 5 cm. Alternatively or additionally, the distance between the radiation exit surface of the illumination source 2 and the target location may be greater than or equal to one of the following values: 1 cm, 2 cm, 3 cm, 4 cm, 5 cm. The distance between the radiation exit surface of the illumination source 2 and the target location may be between 1 cm and 20 cm, preferably between 5 cm and 8 cm.

The illumination source 2 may comprise at least one optoelectronic semiconductor chip for generating the electromagnetic radiation, e.g. a light-emitting diode chip. The radiation emitted by the illumination source 2 may be incoherent radiation. It may be monochromatic, e.g. of light of one specific color. The electromagnetic spectrum emitted by the illumination source 2 may have a peak wavelength in the visible spectral range, e.g. in the red or blue spectral range. The emission spectrum may be narrow. For example, the full width at half maximum of the spectrum (FWHM: Full Width Half Maximum) may be less than 100 nm, e.g. less than or equal to 50 nm.

The electronic control unit 5 is operatively connected to the illumination source 2 and configured to control operation of the illumination source 2 according to an illumination protocol during an illumination session performed with the illumination system 1. The electronic control unit may be part of a computer. The electronic control unit may be a CPU (Central Processing Unit) or a microcontroller. The illumination protocol comprises instructions to operate the illumination source 2 during the illumination session in a plurality of different modes, which are disclosed in detail in FIG. 2.

Figure 2:
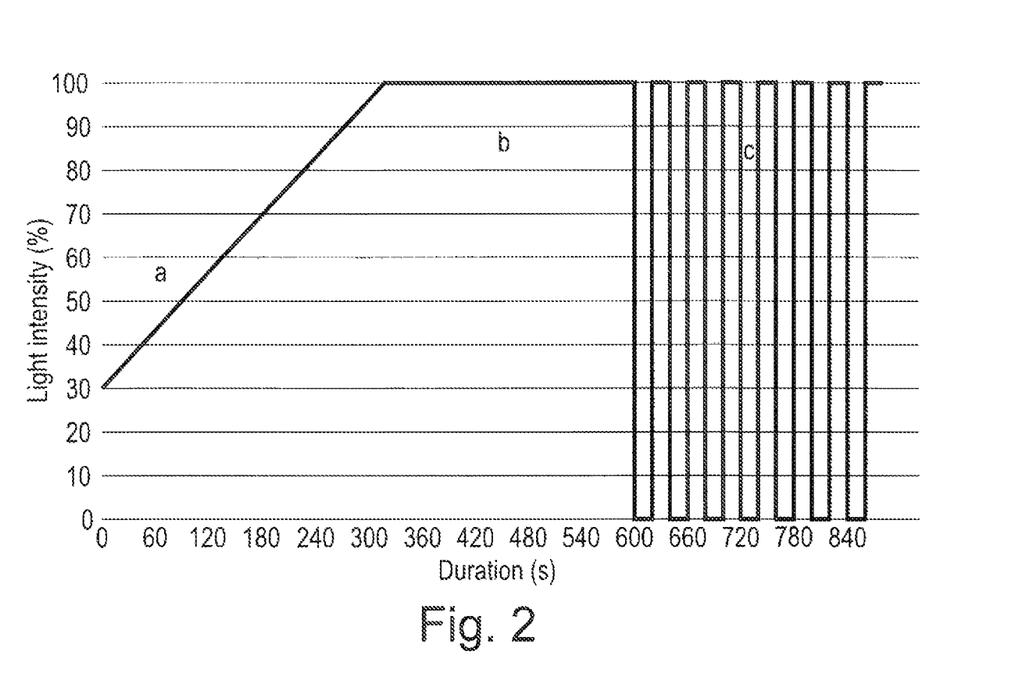
FIG. 2 shows a diagram illustrating an illumination protocol.

FIG. 2 shows a diagram of the illumination protocol with two axes, a first axis representing the duration of the radiation treatment in seconds, and a second axis representing the degree of light intensity in percent. The illumination protocol may govern the entire illumination session.

During a first mode a, which is executed first when using the illumination system 1, the electronic control unit 5 controls operation of the illumination source 2 such that the intensity of the electromagnetic radiation 3 emitted by the illumination source 2 is increased continuously or quasi-continuously from a base intensity B (30%) to a target intensity T (100%) within a first mode time interval.

As illustrated in FIG. 2 a linear ramp is applied which increases the light intensity from 30% to 100% light intensity in the course of 5 or 5.5 minutes. Other durations are possible as well, of course. The intensity at 100% need not be the maximum intensity emittable by the illumination source 2 but rather designates the maximum intensity during the illumination session. Alternatively, the intensity may be increased non-linearly in the first mode a (see FIG. 3, for example). Here, it is preferred that initially the slope is less than later on, which may be advantageous to sensitize the nerve endings.

The first mode a enables provision of a moderate reaction onset to reduce initial photobleaching and promote re-oxygenation of the treated tissue and a slow but continuous increase of the irradiance to trigger a sufficient photodynamic effect, including initial inflammatory reactions that induce vasodilation for even better oxygen supply. The photodynamic effect describes the process during PDT which leads to the destruction of cells, wherein photobleaching describes the effect that the photosensitizer is inactivated by permanent disruption of its chemical structure, e.g. by cleavage of covalent bonds. The photobleaching effect may coincide with temporal oxygen depletion in the target tissue due to a massive initial reaction. This leads to a rapid decrease in oxygen and therefore limits the formation of ROS. In addition, the milder initiation phase allows adaptation of sensory nerve endings in the skin to the stimulus, whereby the perceived pain by the patient is reduced.

After reaching 100% light intensity, a second mode b follows, wherein the electronic control unit 5 controls operation of the illumination source 2 such that the intensity of the electromagnetic radiation 3 emitted by the illumination source is constant or substantially constant for a second mode time interval. As shown in FIG. 2, in the second mode b, the maximum light intensity of the first mode a is maintained. The light intensity may be kept constant for approximately 4.5 minutes. Other durations are possible as well, of course.

This second mode b is important to provide high energy to the target in a relatively short time span and thus keeps the overall duration of the session well below 16 minutes, which is considered acceptable by most patients and physicians regarding the pain burden. Apart from that, the electronic control unit 5 controls the operation of the illumination source 2 such that the illumination source 2 is operated so that the irradiance is stopped or the intensity is reduced after 10 minutes, e.g. by the first darker phase in a subsequent mode (mode c which is discussed below), thereby counter-acting an excessive increase in pain.

In the second mode b the intensity of the electromagnetic radiation emitted by the illumination source is constant or substantially constant. The intensity during the second mode b may be equal to the target intensity T in the first mode.

Then the second mode b is followed by a third mode c. The third mode c is the last mode of the protocol. In the third mode c, the electronic control unit 5 controls operation of the illumination source 2 such that the illumination source 2 is operated such that darker phases and illumination phases alternate for a third mode time interval, e.g. for 6 minutes. The duration of the third mode may be adjusted such that a desired light dose is received at the target surface e.g. 37 $J/cm^2$, which is particularly suitable at least for red light, or 10 $J/cm^2$, which is particularly suitable at least for blue light.

The intensity of the electromagnetic radiation 3 emitted by the illumination source 2 is lower in the darker phases than in the illumination phases. In the example shown, the illumination source 2 does not emit electromagnetic radiation in the darker phases, whereas the illumination source 2 emits electromagnetic radiation 3 in the illumination phases, wherein the light intensity of the illumination phases is identical to the light intensity of mode 2 and the maximum light intensity of mode 1. Of course, the relative intensities may be adjusted as required.

This alternating intensity may be maintained for approximately 4 minutes or more in the third mode c. In the example shown in FIG. 3, the protocol contains seven illumination phases and seven dark phases, which in particular allows for the neuronal activation to wear off to some extent to reduce pain. The duration in the third mode c of one of the darker phases is constant and is equal to the duration of one of the illumination phases. The duration of a phase is 20 seconds each. During the illumination phases the light intensity is kept at 100%. After approximately 14 minutes the illumination is stopped completely and the third mode c is ended. The number of illumination phases and darker phases may vary, of course, as may the absolute or relative duration. Also, instead of not operating the light source to emit no radiation at all during the darker phases, a low intensity, e.g. up to 30% of the maximum intensity may still be tolerable. The intensity in a single illumination phase may be constant or substantially constant.

Due to the alternating phases the target tissue may be provided with enough dark phases to reduce photobleaching and/or to promote re-oxygenation of the treated tissue, which may lead to an increase in efficacy. In addition, the paused illuminations of the last mode c allow for the neuronal activation to wear off to some extent. Therefore the perceived pain is significantly reduced.

This third mode c extends until a total light dose of approximately 37 $J/cm^2$ may be reached. An increased protocol duration while maintaining a light dose of approximately 37 $J/cm^2$ is beneficial, as it is likely to ensure a most balanced rate of oxygen consumption and resupply. The value of 37 $J/cm^2$ particularly holds at least for red light. An increased protocol duration while maintaining a light dose of approximately 37 $J/cm^2$ is beneficial, as it is likely to ensure a most balanced rate of oxygen consumption and resupply.

Alternatively, the third mode c extends until a total light dose of approximately 10 $J/cm^2$ may be reached. The value of 10 $J/cm^2$ particularly holds at least for blue light. An increased protocol duration while maintaining a light dose of approximately 10 $J/cm^2$ is beneficial, as it is likely to ensure a most balanced rate of oxygen consumption and resupply.

If yellow or green light is used, the targeted total light dose may be adjusted appropriately.

The duration of the entire illumination session is expediently kept below 20 minutes or even 16 minutes.

The fractionation of the illumination by dark intervals alternating with higher intensity light, allows re-oxygenation and thus additional photosensitizer activation, especially in the later phases of the illumination when high fluence rates are used, in order to prevent late oxygen depletion. Consequently, the limited treatment time due to pain can be used in a time-efficient manner.

The durations of different darker phases in the third mode c may be equal and/or constant as depicted as may be the durations of different illumination phases in the third mode c. Alternatively, the durations may vary between different darker phases and/or different illumination phases. The same holds for the intensity in the illumination phases, which may be varied, e.g. reduced towards the end of the illumination session. In an embodiment, the duration of the darker phases may be less than the duration of the illumination phases. This results in shorter interruptions of the illumination during the third mode, which may contribute to keep the session duration at a desired time.

The beginning of the operation of the illumination source 2 in the first mode a may define the start of the illumination session and the end of the operation of the illumination source 2 in the third mode c may define the end of the illumination session.

Figure 3:
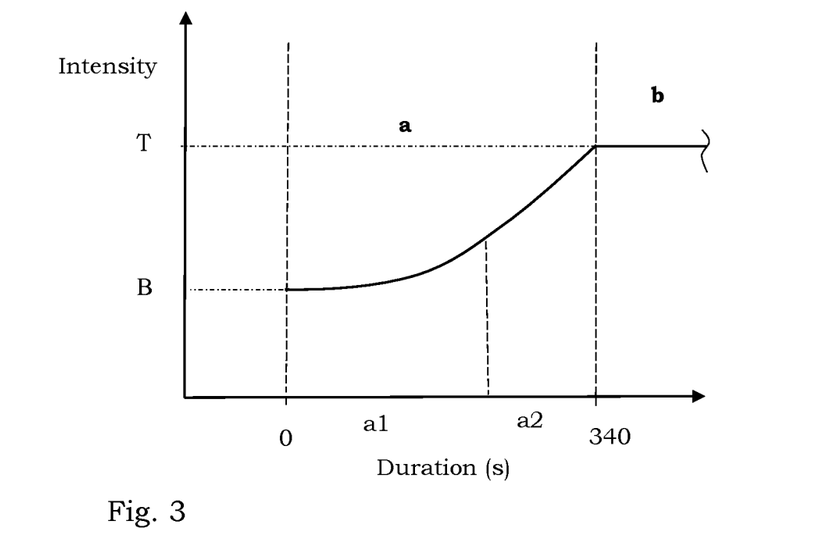
FIG. 3 shows a diagram illustrating a variation of the illumination protocol of FIG. 2.

FIG. 3 illustrates a variation of the illumination protocol shown in FIG. 2. Here, in the first mode of operation (mode a), initially, the intensity is increased non-linearly at a slower rate than later on. In interval a1, the increase may be non-linear, whereas in the subsequent interval a2 it may be linear. The (constant) slope in the linear section may be greater than or equal to every slope in the non-linear section. From mode b, the protocol may be continued as depicted in FIG. 2, for example.

Figure 4:
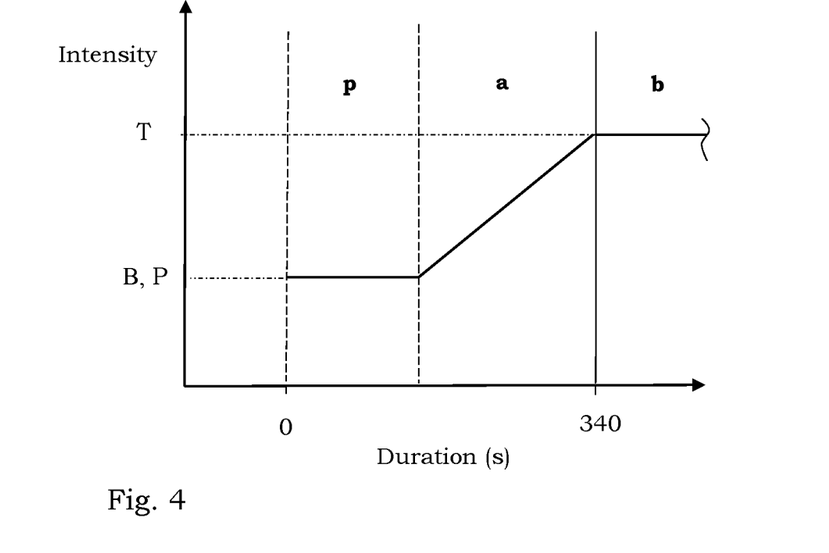
FIG. 4 shows a diagram illustrating yet another variation of the illumination protocol of FIG. 2.

FIG. 4 illustrates another variation of the illumination protocol shown in FIG. 2. Here, a priming mode p is included before mode a is commenced. The duration of the priming mode may be 3 min or less. The intensity P during the priming mode may be equal to the intensity B discussed in FIG. 2. In the embodiments in FIGS. 3 and 4, the onset of the second mode (mode b) is merely as an example shown to be at about 340 s.

The duration of the entire illumination session may be less than or equal to one of the following values: 20 min, 19 min, 18 min, 17 min, 16 min, 15 min, 14 min, 13 min.

The first mode time interval and/or the second mode time interval may be shorter than the third mode time interval. The first mode time interval may be shorter than the second mode time interval or longer.

Above, some durations have been specified for the modes. However, the respective mode—first mode, second mode and/or third mode—may be applied for a time interval which is greater than or equal to one of the following values: 1 min, 1.5 min, 2 min, 2.5 min, 3 min, 3.5 min, 4 min, 4.5 min, 5 min. Alternatively or additionally, the respective mode may be applied for a time interval which is than or equal to one of the following values: 10 min, 9.5 min, 9 min, 8.5 min, 8 min, 7.5 min, 7 min, 6.5 min, 6 min, 5.5 min, 5 min. In this way, the illumination protocol may be adjusted to different situations, for example.

The present disclosure also provides a computer program product, such as a data carrier, e.g. a non-transitory data carrier, or data stream, may contain machine readable instructions which, in particular when loaded in and/or executed by a computer system, e.g. by the electronic control unit 5 thereof, cause the illumination source 2 to be operate according to the above-mentioned protocol.

The illumination system 1 may be used to treat a skin disease or disorder. The skin disease or disorder may be or may comprise a neoplastic skin disease, like actinic keratosis, basal cell carcinoma, squamous cell carcinoma in situ, or warts, acne, wound healing disorders/chronic wounds, bacterial and/or fungal infections or inflammatory skin diseases. However, it should be noted that it may also be used for non-therapeutic methods.

A kit for treating a disease, e.g. a skin disease, such as a neoplastic skin disease may comprise a pharmaceutical substance suitable to be topically applied to the skin in a region to be treated and the illumination system 1 as mentioned above, wherein the illumination system 1 is configured to irradiate a region of the skin to which the substance has been applied. The pharmaceutical substance may be a photosensitizing drug or precursor to such a drug that is excitable by light in the emitted spectrum.

A method for treating a skin disease, e.g. one of the ones mentioned further above may comprise the following steps: applying a pharmaceutical substance, e.g. the prodrug mentioned above, to the surface of the skin in a region which is to be treated; irradiating the region, e.g. with the illumination source 2 according to the method as specified above and/or using the illumination system 1 as specified above.

While applying the illumination protocols as discussed above it is not only expected to increase the efficacy but also to reduce the significance of the pain sensation for the patient/user or the pain perceived overall. A substantial amount of perceived pain is one of the major issues that hinders broad acceptance of PDT by patients. Usually patients report to experience a relatively high amount of pain during the illumination which ranges from mild inconvenience to severe pain up to a point where the treatment has to be aborted. This, of course, has great negative implication for an individual PDT session and PDT treatment as a whole.

The application of the proposed illumination system for photodynamic therapy reduces pain during PDT to a well tolerable level. In addition to this, the acceptance of the treatment itself and the willingness to undergo PDT again is greatly improved when employing this illumination system.

Although PDT is a highly effective treatment method, reoccurrence of the treated disease, e.g. actinic keratosis or another one of the diseases mentioned earlier in this disclosure, is common and thus patients often, although being successfully treated, later develop different lesion at different skin areas and again require medical intervention. Moreover, some patients are not completely cleared after a single PDT session and require a second session. If the first PDT they received was very painful, the completion of a second PDT is highly unlikely despite the fact that it offers supreme efficacy compared to other therapy options.

Consequently, the proposed illumination system and protocol increase the acceptance levels for photodynamic therapy.

One particular illumination system and/or its associated protocol has been described above. However, it should be appreciated that different systems and protocols can be applied as well, especially using features which have been discussed in the introductory section of this disclosure, even if these features are not explicitly described above in conjunction with the figures. Thus, the features discussed in the introductory section are made subject to the exemplary embodiments of this disclosure by explicit reference to these features.

REFERENCE NUMERALS 1 illumination system
2 illumination source
3 electromagnetic radiation
4 target surface
5 electronic control unit
p priming mode
a first mode
b second mode
c third mode

We claim:
1. A method for treating a skin disease by photodynamic therapy comprising the following steps:
 a) applying a pharmaceutical substance to a surface of a skin in a region which is to be treated, wherein the pharmaceutical substance is a photosensitizing drug or precursor to such a drug that is excitable by radiation in an emitted spectrum, leading to the formation of reactive oxygen species that initiate cell death;
 b) positioning an illumination source relative to the region such that a distance between a radiation exit surface of the illumination source and the region is between 5 cm and 15 cm; and
 c) irradiating the region with the illumination source,
 wherein the illumination source is operated according to an illumination protocol during an illumination session, and
 wherein the illumination protocol comprises instructions to operate the illumination source during the illumination session in a plurality of different modes, the modes comprising:
  i) a first mode, wherein, in the first mode, the illumination source is operated such that an intensity of an electromagnetic radiation emitted by the illumination source is increased continuously or quasi-continuously from a base intensity B to a target intensity T within a first mode time interval, and wherein a priming mode of 3 min or less precedes the first mode, wherein, in the priming mode, an electronic control unit controls operation of the illumination source such that the intensity P of the electromagnetic radiation emitted by the illumination source is 0.3 T,
  ii) a second mode, wherein, in the second mode, the illumination source is operated such that the intensity of the electromagnetic radiation emitted by the illumination source is constant or substantially constant for a second mode time interval, and
  iii) a third mode, wherein, in the third mode, the illumination source is operated such that darker phases and illumination phases alternate for a third mode time interval, wherein, in the darker phases the illumination source does not emit electromagnetic radiation whereas the illumination source emits electromagnetic radiation in the illumination phases.

2. The method of claim 1,
wherein a duration of one illumination phase is equal to 60 s and a duration of one darker phase is equal to 30 s.

3. The method of claim 1,
wherein B is less than or equal to 0.4 T.

4. The method of claim 1,
wherein B is equal to 0.3 T.

5. The method of claim 1,
wherein the illumination source is operated in the second mode after the first mode and before the third mode during the illumination session.

6. The method of claim 1,
wherein every mode selected from the first mode, the second mode, and the third mode of operation of the illumination source occurs only once during the illumination session.

7. The method of claim 1,
wherein the electromagnetic radiation has a peak wavelength in the red spectral range.

8. The method of claim 1, wherein the radiation dose is equal to 37 J/cm$^2$.

9. The method of claim 1,
wherein the duration of the entire illumination session is less than or equal to 18 min.

10. The method of claim 1,
wherein the first mode time interval, the second mode time interval, and the third mode time interval is greater than or equal to 3 min.

11. The method of claim 1,
wherein the skin disease is a neoplastic skin disease like actinic keratosis, basal cell carcinoma, squamous cell carcinoma in situ, or warts, acne, wound healing disorders/chronic wounds, bacterial and/or fungal infections, inflammatory skin diseases.

12. The method of claim 1, wherein the intensity of the electromagnetic radiation emitted by the illumination source in a continuous time interval covering the priming mode, the first mode and the second mode is continuously greater than zero.

13. An illumination system for photodynamic therapy which is configured to irradiate the region with the illumination source, according to the method of claim 1.

14. A kit for treating a skin disease, comprising:
a pharmaceutical substance suitable to be topically applied to a skin in a region to be treated, and the illumination of claim 13, wherein the illumination system is configured to irradiate a region of the skin to which the substance has been applied.

* * * * *